United States Patent [19]

Sanderson et al.

[11] Patent Number: 5,492,723

[45] Date of Patent: Feb. 20, 1996

[54] ADSORBENT MEDIUM

[75] Inventors: Alan Sanderson, Newcastle-upon-Tyne; Rod Dove, Swansea; Fang Ming; John Howell, both of Bath, all of Great Britain

[73] Assignee: Sepragen Corporation, San Leandro, Calif.

[21] Appl. No.: 945,652

[22] PCT Filed: May 22, 1991

[86] PCT No.: PCT/GB91/00818

§ 371 Date: Nov. 2, 1992

§ 102(e) Date: Nov. 2, 1992

[87] PCT Pub. No.: WO91/17830

PCT Pub. Date: Nov. 28, 1991

[30] Foreign Application Priority Data

May 22, 1990 [GB] United Kingdom ............... 9011378

[51] Int. Cl.⁶ .................................................. B05D 5/00
[52] U.S. Cl. ............................................. 427/244; 427/339
[58] Field of Search ................................ 427/2, 339, 244

[56] References Cited

U.S. PATENT DOCUMENTS

| | | | |
|---|---|---|---|
| 3,808,305 | 4/1974 | Gregor | 264/331.12 |
| 3,852,224 | 12/1974 | Bridgeford | 260/2.5 M |
| 4,066,387 | 1/1978 | Lewin et al. | 427/245 |
| 4,071,650 | 1/1978 | Gross | 427/2 |
| 4,233,360 | 11/1980 | Luck et al. | 427/244 |
| 4,310,593 | 1/1982 | Gross | 427/2 |
| 4,332,916 | 6/1982 | Thill | 521/25 |
| 4,374,204 | 2/1983 | Alexandrov et al. | 521/28 |
| 4,415,388 | 11/1983 | Korpman | 427/244 |
| 4,468,428 | 8/1984 | Early et al. | 428/221 |
| 4,559,243 | 12/1985 | Pässler et al. | 427/244 |
| 4,711,793 | 12/1987 | Ostreicher et al. | 427/245 |
| 5,002,984 | 3/1991 | Rainer | 524/30 |
| 5,071,880 | 12/1991 | Sugo | 427/244 |
| 5,116,552 | 5/1992 | Morita et al. | 427/244 |

FOREIGN PATENT DOCUMENTS

| | | |
|---|---|---|
| 0316642 | 5/1989 | European Pat. Off. . |
| 1226448 | 3/1971 | United Kingdom . |

OTHER PUBLICATIONS

Webster's Ninth New Collegiate Dictionary, p. 1139, 1986.
International Search Report of European Patent Office of PCT/GB91/00818 dated Aug. 23, 1991.
PCT Int'l Preliminary Exam Report of UK Patent Office of PCT/GB91/00818 dated Mar. 23, 1992.

Primary Examiner—Diana Dudash
Attorney, Agent, or Firm—Medlen & Carroll

[57] ABSTRACT

A cross-linked flexible sponge absorbent medium containing substantially uniformly distributed fibrous reinforcement is prepared under such conditions that swelling of the sponge is controlled to a water retention value of 2 to 6; and simultaneously or subsequently, the cross-linked sponge is reacted with a reagent which introduces functional groups into the modified cross-linked sponge. There is also provided apparatus having an inlet for liquid, an outlet for liquid so as to define a path for liquid flow between the inlet and the outlet, an adsorbent medium, obtainable by the above method, being positioned across the liquid flow path in the apparatus.

10 Claims, 3 Drawing Sheets

ADSORBENT MEDIUM

The present invention is concerned with sponge adsorbent media having functional groups chemically bonded thereto.

There are two broad ways of making cellulosic materials in the form of flexible sponge and having functional groups (such as ion-exchange groups) chemically bonded to the cellulose. In one method, as described in GB 914421, a pre-formed flexible cellulosic sponge is modified by reaction with a reagent which introduces ion-exchange groups (such as orthophosphoric acid or sodium chloroacetate). GB 1387265 discloses ion-exchange cellulosic material prepared by reaction of cellulose with a reagent which introduces ion-exchange groups, followed by regeneration into the desired physical form, among which is sponge.

GB 1226448 discloses a method of making an ion exchanger, which comprises the introduction of cross-linking residues into regenerated cellulose together with or followed by introduction of cation or anion exchange groups into the cellulose. The cellulose is typically obtained from viscose; no preferred physical form for the cellulose is specified (i.e. the cellulose may be used in a variety of physical forms such as rod, filament, yarn, woven cloth, flakes, beads, granules, powder, sponge, tube or sheet).

The present invention is concerned with a method of preparing sponge adsorbent media having a pre-determined porous structure and which method involves modification of a flexible sponge.

Hydrophilic cellulosic chromatographic media have been widely used for the isolation or separation of macromolecules, such as proteins, both in the laboratory and on a commercial scale. However, sponge adsorbent media have not been used greatly in commercial chemical separation operations (such as ion-exchange separation techniques), probably because of the absence of any sponge adsorbent media possessing the required porous structure and the resulting difficulties of ensuring adequate contact between the liquid being treated and the sponge. For this reason, particulate and granular media are generally used, despite the disadvantages associated with the use thereof such as slow flow rates, plugging of the bed, and maldistribution of flow and also the need for considerable skill in filling a column to avoid channelling.

The mass transfer rate of substances being treated by means of adsorbent media is generally diffusion limited. The adsorption reaction at the surface of adsorbent media is fast, whilst limiting processes for adsorption and elution are the film diffusion resistance around the matrix and the pore diffusion resistance within it. Higher flow rates will reduce the resistance of film diffusion and hence increase productivity by decreasing process time. The resolution of ion-exchange chromatography requires the column to have a certain length, the flow rate being inversely proportional to column length. When recovering a biological molecule present in very low concentration in a large volume of feedstream, flow rate and capture efficiency are the major factors to be optimised.

We have now devised a method of producing cellulosic sponge adsorbent media having superior flow properties and adsorption and desorption kinetics, and which are also specifically modified so as to be suitable for use as chromatographic adsorbents.

According to the invention, there is provided a method of preparing a sponge adsorbent medium, which method comprises: preparing a cross-linked flexible sponge containing substantially uniformly distributed fibrous reinforcement, under such conditions that swelling of said sponge is controlled to a water retention value of 2 to 6; and, simultaneously or subsequently, reacting the resulting cross-linked sponge with a reagent which introduces functional groups into the modified cross-linked sponge.

The fibrous reinforcement preferably comprises cotton linters, typically present in an amount of about 2 to 50% by weight; materials such as jute, cotton fibres, flax or other hydrophilic fibres may alternatively be used. Such hydrophilic fibres preferably contain free hydroxy which are reactive with the cross-linking agent used; the fibres are preferably cellulosic. In some embodiments, nylon or other hydrophobic fibres may be used, in addition to or in replacement of the hydrophilic fibres. The fibrous reinforcement used according to the invention provides a supporting structure which permits chemical modification of the pre-formed sponge without complete disintegration, and also provides the sponge with sufficient rigidity for the latter to be suitable for use as a chromatographic adsorbent. (The sponge materials prepared as described in GB 914421 and 1387265 would be too compressible to be used as chromatographic adsorbents.)

Preferably the flexible sponge is a polymeric material which typically comprises any of the following: polysaccharides (such as regenerated cellulose or cross-linked dextrans), polyvinyl alcohol, polystyrene or polyurethane. Hydrophilic sponge polymers are preferred however, because hydrophobic materials are known to be less suitable for chromatographic work with proteins. This is because irreversible binding and denaturation of the protein often occurs as a result of the use of such hydrophobic materials. Particularly preferred hydrophilic sponge polymers are polysaccharides (such as regenerated cellulose, which can be solubilised and then regenerated in a number of ways). Typically this can be done either via an intermediary product such as an ester, by the viscose process, or by dissolution in cuprammonium hydroxide. Regenerated cellulose is also particularly preferred because the ion exchange groups can be advantageously located in easily accessible sites such as the pore surfaces (as opposed to being buried within the body of the adsorbent medium) and this helps in achieving fast kinetics of adsorption.

In the case of other polymers, such as vinyl polymers and styrene polymers and polyurethane polymers (such as those derived from polyisocyanates and polyethers or polyamides), it may be preferable to mix the pore forming agent with the monomers or prepolymers, so that the polymerisation (and cross-linking) takes place in situ.

The sponge body may be further supported by a rigid mechanical support such as wire or an open mesh, typically of nylon or other hydrophobic fibres, although in some embodiments, the body may contain one or more hydrophilic meshes made from such material as cotton scrim or flax. Therefore in one embodiment, the flexible cellulosic sponge may be moulded about the mechanical support before regeneration of the cellulose. In another embodiment, the mechanical support may be introduced into the flexible cellulosic sponge after regeneration of the cellulose and may be held in place by the use of a suitable adhesive.

The nature of the porous structure of the flexible sponge to be used in a method according to the present invention, is determined by the nature of the chromatographic separation in which it is required to be used, and can therefore be varied so as to be suitable for its required use. Typically, however, the porous structure of the sponge used in a method according to the invention, has a total void volume in the range of about 70 to 98% (preferably 80 to 96%) of which the fractional voidage is no more than 95% thereof.

It is generally preferred that the flexible sponge contains primary and secondary pores. The primary pores are interconnecting pores which are dimensioned so as to allow the free passage of the process liquids throughout the sponge. The secondary pores are provided in the walls of the primary pores, the former housing the majority of chromatographic adsorption sites. It is beneficial if the rate of diffusion of the chromatographic solution in and out of the pores is rapid. It is therefore preferable that the walls between the primary pores are thin and rich in suitably sized secondary pores to maximise kinetic rates.

The production of a porous structure comprising interconnecting pores generally involves contacting a solution of the sponge-forming polymeric material with a pore-forming agent such as a gas. In the case where the polymeric material is cellulose, the sponge-forming polymeric material is contacted with the gas either prior to, or simultaneous with, regeneration of the sponge. Either a gas, or gas forming materials, is/are introduced into the polymeric solution. Examples of gas-forming materials include solids, volatile liquids, chemical reagents (such as calcium carbonate and acid), thermally decomposable materials (to cause evolution of a gas by, for example, decomposition of bicarbonate) or biological agents (such as dextrose and yeast).

It is particularly preferred that the gas-forming materials are solid reagents such as powders, crystals, oils, waxes or ground biological tissue. The use of solids as precursors for the gaseous pore-forming agents is more suitable for the production of primary pores than secondary pores; this is because it is often extremely difficult to produce solid particles of a sufficiently small size generally required for the production of secondary pores. In the case where the polymeric material is cellulose the reagent may be removed either after or during the regeneration of the cellulose into solid form, the removal typically involving either treatment with an acid, an alkali, or an enzyme, the use of electromagnetic energy or solvent action.

A particularly preferred method of producing a sponge having an interconnecting porous structure involves use of a xanthate; the latter method is preferred because the size of pores produced by gas given off by the xanthate can be varied by varying the degree of substitution of the latter.

A further preferred method of producing a sponge having an interconnecting porous structure involves the use of crystals of hydrated sodium sulphate where particles of varying sizes can again be used. For a high resolution on a laboratory scale, crystals of hydrated sodium sulphate having a particle size in the range from 200 to 400 microns can be used to make the interconnecting pores. For a larger scale commercial separation requiring high flow rates, crystals of hydrated sodium sulphate having a particle size of 1500 to 3000 microns can be used. It is particularly difficult to use hydrated sodium sulphate with a particle size less than 100 microns to form correspondingly sized pores in the sponge. However, when it is required to produce a sponge having a pore size in the order of 100 microns other solids such as calcium carbonate may be used.

The actual volume of the primary pores (i.e. fractional voidage) is dependent on the amount of primary-pore forming agent introduced into the sponge-forming polymeric solution and as hereinbefore described can take any value up to 95% of the total void volume.

The thickness of the walls of the primary pores largely depends on the quantity of primary pore forming agent which is mixed with the solution of sponge forming polymeric material. Among other factors, the minimum wall thickness will depend on how closely the particles of the primary pore forming agent fit together. The overall amount of functional groups which can be introduced per unit volume into the flexible sponge will generally be increased as the density of the sponge is increased. The thickness of the primary pore walls may be varied depending on the required use of the sponge adsorbent medium. For example, if the medium is used for the processing of mineral ions, then a thick wall can be used because the diffusion rates for mineral ions are fast. However, if the medium is used for the chromatography of macromolecules such as proteins, then a thin wall would be preferred because of the slow rate of diffusion of the macromolecules through the wall. It is not possible however to obtain uniform wall thicknesses within a sponge medium (e.g. a cellulosic sponge medium is known to have a wall thickness ranging between 5 and 45 microns). In a method according to the present invention, the resultant adsorbent medium generally comprises an interconnecting porous structure where the primary pore wall thickness is typically in the range of about 2 to 300 microns.

In the use of the porous sponge media, it is desirable to achieve plug flow (which is associated with the best quality separations) and to minimise axial dispersion or back mixing. A narrow range of primary pores sizes is therefore preferred, and overlarge pores which can be associated with non uniform flow should be eliminated.

The secondary pores may be naturally occurring in the polymer as a result of variation in its density or may be formed by the use of a pore forming agent or agents which are generally used in conjunction with the primary pore forming agent. Typically the secondary pores are smaller than the primary pores and may be formed by any of the following methods.

A solution of the polymeric material may be mixed with a removable reagent having individual particles of a predetermined size, so as to produce a flexible sponge having a desired secondary pore structure (i.e. a structure having a pore size determined by the reagent particle size). A liquid (probably immiscible with the polymer solution) can be added to the polymer solution which upon mixing forms continual channels within the liquid polymer. Alternatively, the density of the polymer solution (in this case cellulose) may be lowered by the addition of a suitable solvent so that when the cellulose is regenerated the resulting sponge has an open pore structure. Suitable methods of removing the added gas or liquid are as above.

The secondary pores may of course be produced by contacting the polymer solution with a solid pore-forming agent; however this method is generally less successful in producing secondary pores of a required size (as previously described).

The resulting medium may have higher flow rates than conventional adsorbent media. For example, when used in a column of height 4 mm and an internal diameter of 43 mm, under a pressure of one bar, flow rates in excess of 50 meters per hour may be achieved (for example about 90 meters per hour). This compares with good commercially available media (such as those commercially available under the trade names Whatman CM52 and Indion HC2, both of which are carboxymethyl celluloses), where under similar conditions, flow rates of less than 40 meters per hour are achievable.

In the method according to the present invention, cross-linking is particularly important in maintaining the predetermined porous structure and also to protect the porous sponge and derivatives thereof against deterioration due to chemical and physical attack. It is preferred that cross-linking of the sponge comprises contacting the sponge with a liquid having dissolved therein a chemical cross-linking agent for the sponge. In the case of a cellulose sponge the cross-linking agent can be added either during or after regeneration of the cellulose sponge and may be added in one or more stages. A preferred embodiment however involves the addition of the cross-linking agent to the solution of sponge forming cellulosic material during the regeneration process. In this way the pores are substantially maintained at their predetermined size. Alternatively cross-linking is carried out after regeneration is complete. In this case the porous cellulose sponge is first swollen to give the desired pore size, and then cross-linked to hold the porous structure.

The liquid having the chemical cross-linking agent dissolved therein may be an aqueous alkaline solution, generally comprising sodium hydroxide. Such an aqueous alkaline solution typically contains sodium hydroxide in an amount of 0.5 to 7 molar, preferably slowly raised from 0.7 to 5 molar over the period of one hour. Alternatively a unimolar solution can be used over the same time period. If the molarity of the solution is either too high or too low, the flow rate of liquid through the resultant adsorption medium and the mass-transfer kinetics are impaired. If too high, undesirable gel formation may result, with deleterious effect on the flow rate.

The nature of the cross-linking agent will depend on the flexible sponge material. In the case of polysaccharides such as cellulose a polar cross-linking agent may be used which is soluble in aqueous media. Examples of suitable such cross-linking agents include formaldehyde, dichlorhydrin, epichlorhydrin, dibromomethane, bis-epoxypropyl ether, a 1,4 butane diol bisepoxy ether, dialdehydes such as glyoxal, and divinyl compounds such as divinylsulphone. Preferred cross-linking agents are dichlorhydrin (which is most preferred) and epichlorhydrin.

The cross-linked sponge may be further treated with, for example hot sodium hydroxide solution. This will solubilise parts of the sponge (particularly low molecular weight fractions) which have not been cross-linked and therefore open up the sponge structure. However, the reaction conditions are chosen according to the nature of cross-linking agent, for example epoxy compounds such as epichlorohydrin are preferably used in an alkaline medium, whereas aldehydes such as formaldehyde are preferably used in an acidic medium.

In the case where the sponge is formed in situ then the cross-linking agent may be part of the sponge forming process (such as the use of divinyl benzene to cross-link polystyrene).

It is recognised that the nature of the flexible sponge, including the general porous structure, may depend on a wide range of factors which influence the manufacturing system. For example changes may be made to the concentration, degree of polymerisation, or viscosity of the polymer. Agents (such as surfactants) likely to effect the secondary and primary pore structure may be added.

The reagent which is subsequently reacted with the cross-linked sponge may be one which introduces ion-exchange groups. Examples of such reagents are compounds containing amino, alkylamino or quaternary ammonium groups (when it is desired to produce an anion exchange resin), or compounds containing sulpho, phospho or carboxyl groups (when it is desired to produce a cation exchange resin).

Examples of the former type of compound are diethylaminoethyl chloride (optionally followed by reaction with bromoethane to produce the corresponding quaternary derivative), chlorohydoxypropyl trimethyl ammonium chloride, glycidyltrimethylammonium chloride, polyethyleneimine, di-(hydroxyethyl)-aminoethyl chloride and p-morpholino ethyl chloride; examples of the latter type of compound are chloroacetic acid, chlorohydroxypropane sulphonic acid, sodium bisulphate, bromoethane sulphonic acid, hydroxyethane sulphonic acid, chloroethane sulphonic acid, chlorosulphonic acid, chloromethane sulphonic acid and 1,3-propane sulfone.

Other types of functional groups which may be introduced by the reagent which is reacted with the cross-linked sponge include metal chelates, antibodies (such as IgG), antigens (such as Protein A), dyes, lectins, or groups which can fix biologically active materials such as enzymes. An example of the latter type of group results from the reaction of the sponge successively with carbonyl diimidazole, p-amino-benzamide and hexanoic acid; an example of the introduction of chelate groups is by successive reaction with a diglycidyl ether, sodium borohydride (to produce epoxy groups), iminodiacetic acid, and a zinc or copper salt.

The resulting sponge adsorbent medium can be further treated so as to modify the pore surface chemistry. For example the pore surface can be coated with a materials such as polyethylene imine or DEAE dextran, or chemically grafted to produce polymers such as polyacrylic acid, polyethylene imine or materials such as phosphatidyl choline derivatives so that they occupy some part of the space inside the pore.

GB 1387265 describes the production of an ion exchange sponge by introducing ion-exchange groups before regeneration of the cellulose. The method according to the present invention allows such ion exchange groups to be introduced into regenerated cellulose sponge. According to the present invention the ion-exchange groups can be introduced into the regenerated cellulose sponge by spraying or soaking of the cellulose sponge with a suitable reagent. Any excess reagent can be removed by the action of a roller, under vacuum or by heating. The latter may be effected by convective or radiant heat processes such as curing, or microwave or radio frequency radiation. Alternatively the cellulose sponge may be placed in a housing and the reactive solutions passed through the sponge. Heating may be affected by the use of a pre-heated inert liquid or gas.

The body of flexible sponge material used in accordance with the present invention may be in the form of a block, an annulus, a continuous sheet, a rolled sheet, a disc, a tape, a rod, a pad or the like. Although it is possible to use the adsorbent medium in a free form, it is generally used in apparatus having an inlet for liquid, an outlet for liquid (which may in some embodiments, be the same as the inlet or, in other embodiments spaced from said inlet) so as to define a path for liquid flow between the inlet and the outlet, said adsorbent medium being positioned across said liquid flow path.

The adsorbent medium is generally used in block form in the apparatus which means that there is the possibility that liquid could flow between the internal wall of the apparatus and the adsorbent medium. This problem may be overcome in a variety of ways such as the use of a sealant or an adhesive or both. A preferred embodiment however is to use the adsorbent medium under compression across the liquid flow path such that liquid flows from the inlet through the adsorbent medium.

The degree of compression is preferably such that the lateral dimension is at least 1%, more preferably at least 3% (such as 3 to 10%) less than the corresponding dimension of the adsorbent medium in unrestrained form.

The use of the adsorbent medium under lateral compression in the apparatus according to the invention is such that short-circuiting (that is, passage of liquid through the apparatus without contact with the adsorbent medium) is avoided.

In one embodiment of the present invention, the adsorbent medium may be in the form of a flexible block typically in the form of a cylinder with the inlet and/or outlet connected to the axial core to the cylinder. It is preferred that the adsorbent medium should be under substantially uniform compression throughout its volume.

The apparatus may be primed for use by inserting the adsorbent medium in the liquid path in at least partially dehydrated form, and allowing the adsorbent medium to undergo hydrophilic swelling such that it is laterally compressed by the walls of the liquid path. Alternatively, the adsorbent medium, in hydrophilic swollen state, may be preliminarily compressed prior to insertion in the liquid path followed by partial release of the compressive restraint when the adsorbent medium has been inserted in the liquid path. In a further alternative, the adsorbent medium may be compressed after insertion into a liquid path by compressive means acting on one or more of the walls defining the liquid path.

When the adsorbent medium is in the form of discs or pads, a plurality of such discs or pads can be stacked in a column for use, for example in chromatographic separation, when material to be separated could be selectively eluted from different pads or discs, or parts thereof, in the stack.

In one embodiment of the invention in which a stack of such discs or pads are employed, it may be advantageous to provide indicator means to indicate different levels in the stack. For example, different colours can be employed to indicate different levels in the stack; discs from different levels may be removed from the stack and treated separately for isolation of respectively fractionated material therefrom.

The apparatus and adsorbent medium according to the invention may be used in any conventional adsorption process, such as the isolation of proteins (for example, from dairy or soya whey), or mineral ions, adsorption of polyelectrolytes (e.g. humic acid), or radioactive reagents by ion-exchange from liquid phase material, affinity chromatography, or immobilisation of enzymes, or lysozyme separation.

The apparatus according to the invention may be provided with means for compression of the adsorbent medium, whereby the latter can be successively compressed and decompressed, for example, following an adsorption phase and/or following a washing phase. Material adsorbed by the ion-exchange material can be adsorbed either in the compressed state or in the decompressed state (in the latter case the desorption phase is preferably followed by successive compression and decompression). When desorption takes place with the adsorption medium in the compressed state, this may involve an adsorption phase with a relatively high void percentage, followed by a desorption phase with a relatively low void percentage.

The use of successive compression/decompression phases enables a high degree of liquid-solid contact to be obtained in the adsorption phase, followed by efficient desorption of treated liquid; the yield of materials such as polyelectrolytes can be thereby increased, and the volume of liquid product can be decreased (that is, its concentration can be greater).

For some purposes, the adsorbent medium may be used partially compressed throughout, with remarkably little change in flow characteristics compared to the uncompressed medium. This enables improved volumetric efficiency to be obtained (that is, more adsorbent medium can be employed per unit volume, without substantial impairment of liquid flow).

According to another aspect of the invention, therefore, there is provided a method of isolating material from a liquid phase which comprises flowing liquid from the inlet to the outlet of apparatus according to the invention so as to cause said material (which is typically a polyelectrolyte material, a protein or the like) to be adsorbed from the liquid, terminating the flow of liquid, and compressing the adsorbent medium. This compression allows elution with a lower volume of desorbent.

The adsorbent medium need not necessarily be used vertically; for example, in some embodiments, it may be used horizontally (unlike, say, conventional granular ion-exchange media, which must be used in vertical orientation).

Figure 1:
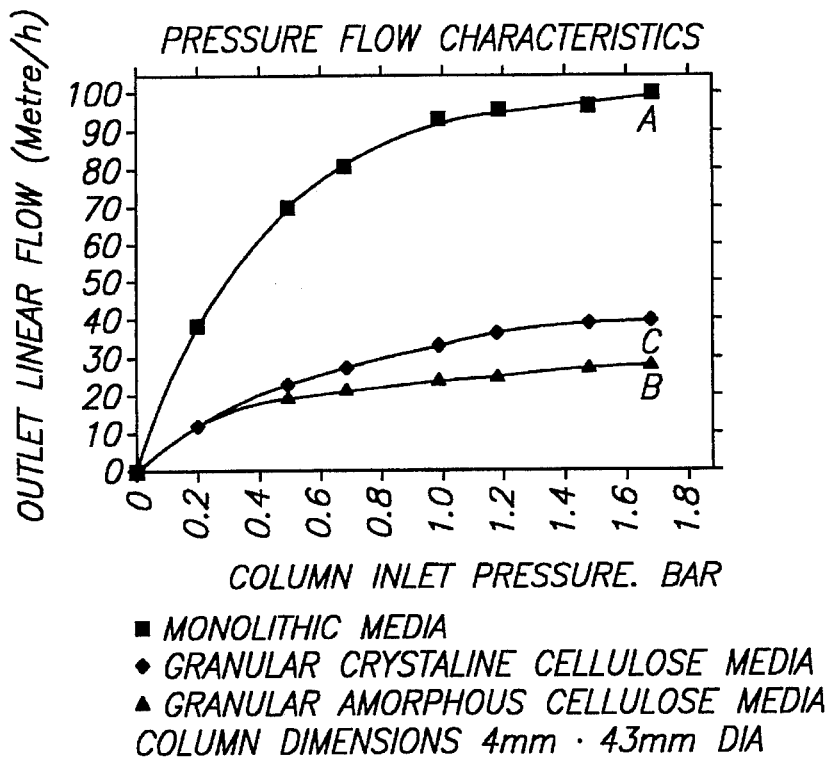
FIG. 1 is a graph showing comparative flow rates obtainable using a cellulosic medium produced according to the present invention in comparison with other cellulosic media.

According to the invention the sponge adsorbent medium may be reduced to a powder which may then be reconstituted into a solid form, e.g. by the use of an adhesive.

The invention will now be illustrated by reference to the following Examples and Figures, which do not limit the scope of the invention in any way.

Examples 2, 3, and 4 illustrate methods of treating a cross-linked cellulose sponge obtained by the method of Example 1, with a reagent which introduces functional groups. Examples 5 to 12 illustrate the properties of a resultant treated sponge.

EXAMPLE 1 a). Production of Viscose 500 g of alkaline cellulose was prepared containing 137.5 g of cellulose, 77.5 g of NaOH and 285 g of water. The average degree of polymerisation of the cellulose had been reduced to approximately 200 by alkaline oxidative degradation. This was transferred to a z-arm mixer and reacted with 90 g of carbon disulphide at 32° C. for 60 minutes. 250 g of 19% NaOH and 1275 g of chilled water were then added to make viscose.

The viscose was then further processed according to any of the following methods to produce a cellulose sponge from which anion and cation exchangers or affinity material could be produced. In each case a flat sheet (although other forms such as a block or annulus could be produced) of porous adsorbent material with a thickness of approximately 5 mm was produced, which was washed and treated with 0.1M HCl to dissolve the calcium carbonate, and then further washed and de-watered. In method 2, 50 g of the porous sheet material was further treated with dichloropropanol.

METHOD 1

To 1500 g of the viscose was added: 32 g of cotton linters and 5000 g of crystals of sodium sulphate decahydrate (particle size range from 1000 to 3000 microns). The resulting mixture was blended to produce a paste. The paste was then moulded between 2 plates of perforated stainless steel and regenerated in sodium sulphate solution at 95° C.

METHOD 2

To 1500 g of the viscose was added: 32 g of cotton linters, 3900 g of crystals of sodium sulphate decahydrate (particle size range from 200 to 400 microns), and 1000 g of powdered calcium carbonate (particle size less than 2 microns). The resulting mixture was blended to produce a paste. The paste was then moulded between 2 plates of perforated stainless steel and regenerated in sodium sulphate solution at 95° C.

b). Production of Cross-Linked Cellulose Sponge

METHOD 3

To 1500 g of the viscose was added: 15 ml of epichlorohydrin, 80 g of cotton linters, 5000 g of crystals of sodium sulphate decahydrate (particle size range from 1000 to 3000 microns), and 1000 g of powdered calcium carbonate (particle size less than 2 microns). The resulting mixture was blended to produce a paste. The paste was then moulded between 2 plates of perforated stainless steel and regenerated in sodium sulphate solution at 95° C. The resulting regenerated material had a water retention value of 3.2 and a porous volume of 91%. In this method cross-linking was achieved simultaneous with regeneration of the sponge.

METHOD 4

50 g of cellulose sponge produced according to method 1 was treated with 0.6 to 5.0 M NaOH over a one hour period with 250 to 2000 ml of liquid containing 1% to 5% v/v of dichlorohydrin. The sponge was subsequently cured at 60° C. for up to 1 hr. The resulting material was a porous cross-linked cellulose sponge from which anion and cation exchangers or affinity material may be produced. The resulting material had a water retention value of 3.4; similar runs can be operated with water retention values in the range 2 to 6. The porous volume of the resulting material was determined by column tracer flow using acetone, and was found to be 92%; similar runs can be operated to give porous volumes in the range 70 to 98%. A sample of the material was cut to obtain a clean cross-section and freeze dried to remove water. The latter was then examined by SEM. The average primary wall thickness was estimated to be about 20 microns; similar runs can be operated to give average wall thicknesses in the range 2 to 300 microns. The variance in wall thickness could be achieved by changing either the cellulose content of the viscose or the amount of cotton linters and pore forming agent in the paste.

METHOD 5

50 g of cellulose sponge produced according to Method 2 was subjected to cross-linking as in Method 4. The resulting material had a water retention value of 3.3%, a porous volume of 94% and a primary wall thickness of 7 microns.

EXAMPLE 2

Carboxymethyl cellulose was produced by taking 50 g of a cross-linked cellulose sponge, obtained by method 4 of Example 1, and adding thereto 400 ml of a solution of 5M NaOH and 80 g of sodium chloroacetate and maintaining the mixture at 100° C. for 1 hr. The resultant medium has a protein capacity of 2 g per dry gram of sponge with a maximum liquid flow in excess of 40 meters per hour and also a water retention value of 3.2.

EXAMPLE 3

Sulphopropyl cellulosic sponge is produced by taking 50 g of a cross-linked cellulose sponge, obtained by method 4 of Example 1 and adding thereto 1000 ml of a solution containing 5M NaOH and 590 g of the sodium salt of chlorohydroxy propane sulphonic acid and maintaining the mixture at a temperature of 100° C. for 3 hrs. The resultant cellulosic sponge material has a protein capacity of one gram per dry gram with a maximum liquid flow rate in excess of 40 meters per hour and a water retention value of 3.4.

EXAMPLE 4

Quaternary methyl ammonium cellulosic sponge is made by taking 50 g of a cellulose sponge, obtained by method 4 of Example 1 and adding thereto 900 ml of liquid containing 5M NaOH, 164 g of chlorohydroxy propyl trimethyl ammonium chloride and 1.74 g of sodium borohydride and maintaining the mixture at 50° C. for 2 hrs. The resultant cellulosic sponge material has a protein capacity of 1.5 g per dry gram with a maximum liquid flow rate in excess of 40 meters per hour and a water retention value of 3.3.

EXAMPLE 5

FIG. 1 shows comparative flow rates through three cellulosic media. Curve A corresponds to a medium obtained according to Example 4, Curve B corresponds to CM52 and Curve C corresponds to Indion HC2. The flow rates were measured using a column of height 4 mm and an internal diameter of 43 mm, under a pressure of one bar. As seen in FIG. 1, a flow rate of about 90 meters per hour is obtainable using a cellulosic medium produced according to the present invention, whereas flow rates of less than 40 meters per hour (about 20 and 35 respectively) were obtained using CM52 and Indion HC2.

Figure 2:
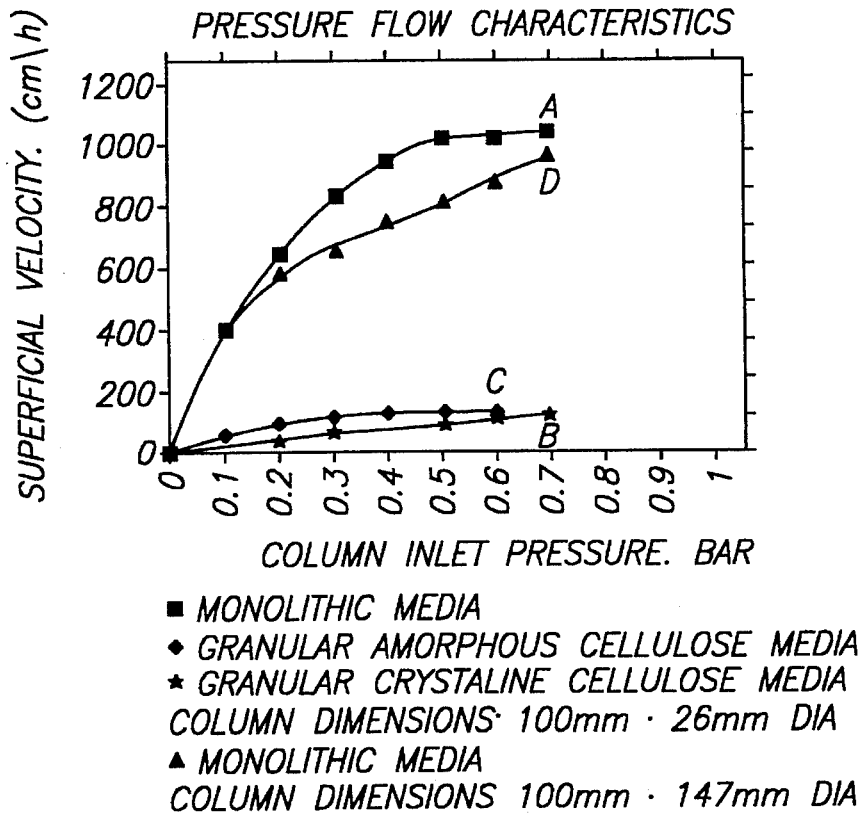
FIG. 2 is a graph showing comparative velocities through a cellulosic medium according to the present invention in comparison with other cellulosic media.

FIG. 2 shows comparative velocities through cellulosic media. A column of 100 mm×26 mm was packed with a cellulosic medium obtained according to Example 4 and a maximum flow rate therethrough of 10 meters per hour was achieved (Curve A), the column was similarly packed with CM52 and HC2 both achieving maximum flow rates of less than 1 meter per hour (Curves B and C respectively).

A column of 100 mm×147 mm was also packed with a cellulosic medium obtained according to Example 4 and a maximum flow rate of 9 meters per hour was obtained (Curve D).

Figure 3:
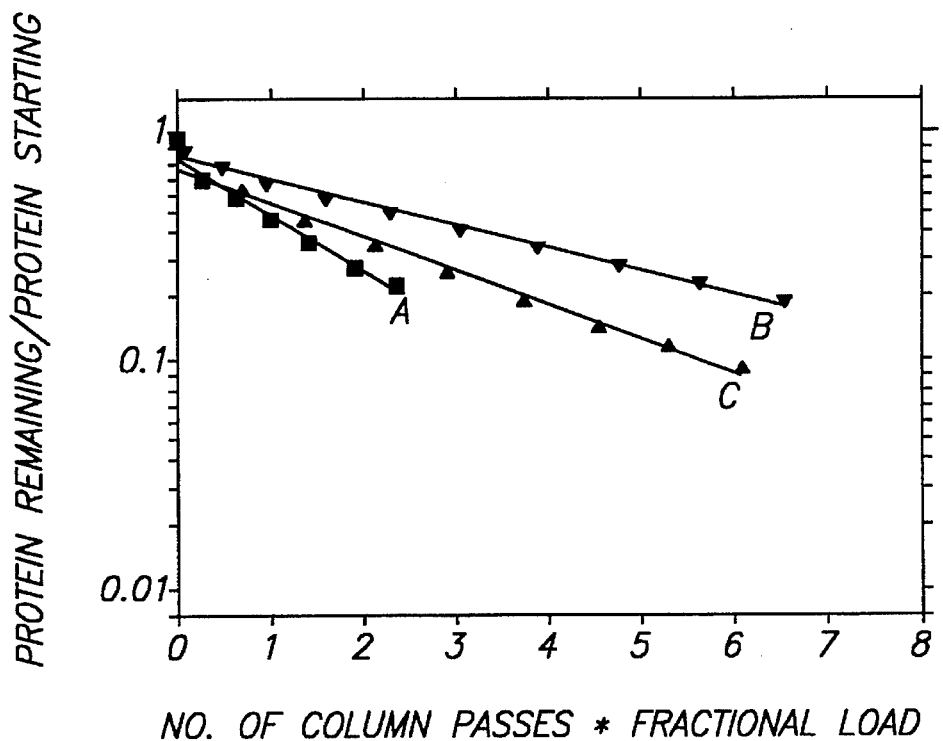
FIG. 3 is a graph showing a comparison of the adsorption kinetics of regenerated cellulosic sponge according to the present invention in comparison with the adsorption kinetics of other cellulosic media.

Referring to FIG. 3, there is shown a comparison of the adsorption kinetics of regenerated cellulosic sponge obtained according to Example 4 with the adsorption kinetics of HC2 and CM52 cellulosic media. All three media were arranged in a 30 mm×25 mm via column adsorbing protein in recirculation batch mode at a flow rate of 4 meters per hour. The dimensionless rates for the three media were 0.35, 0.15 and 0.1 respectively.

Figure 4:
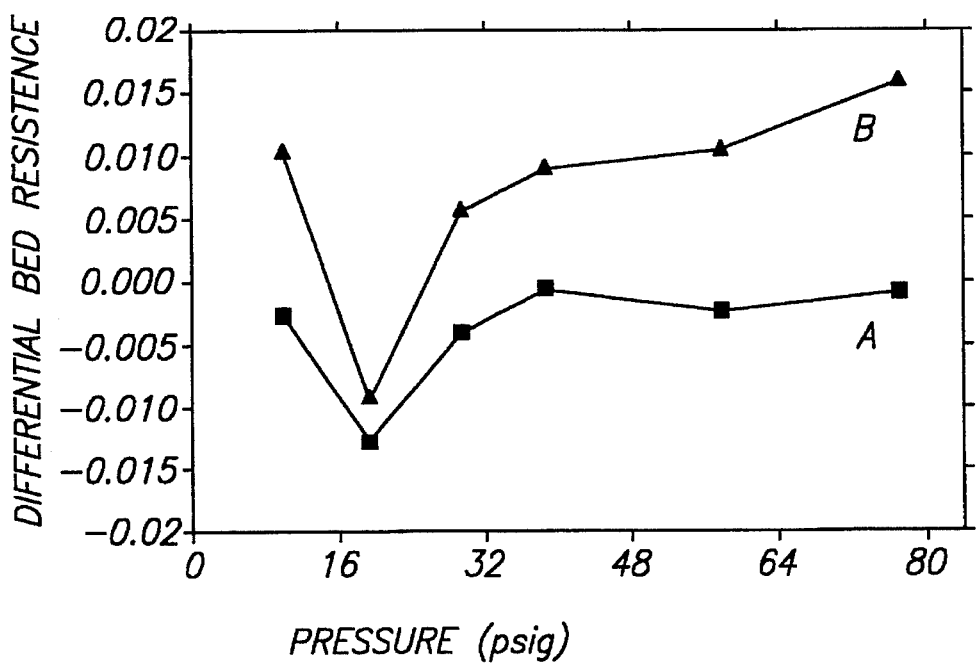
FIG. 4 is a graph showing the effect on bed resistance when a sponge according to the present invention is compressed by differing factors.

FIG. 4 shows the effect on bed resistance when sponge made according to the invention is compressed by a factor of 1.25 (Curve A) and a factor of 2 (Curve B).

EXAMPLE 6

Cross-linked porous regenerated cellulose was made according to Example 1 and converted to carboxymethyl cellulose according to Example 2. This was then used for the separation of ovalbumin, conalbumin and lysozyme from fresh egg white, in a single step. The conalbumin and lysozyme were assumed to be 95% pure by gel electrophoresis and the overall process had a productivity in excess of 80 kg/m/hr.

Figure 5:
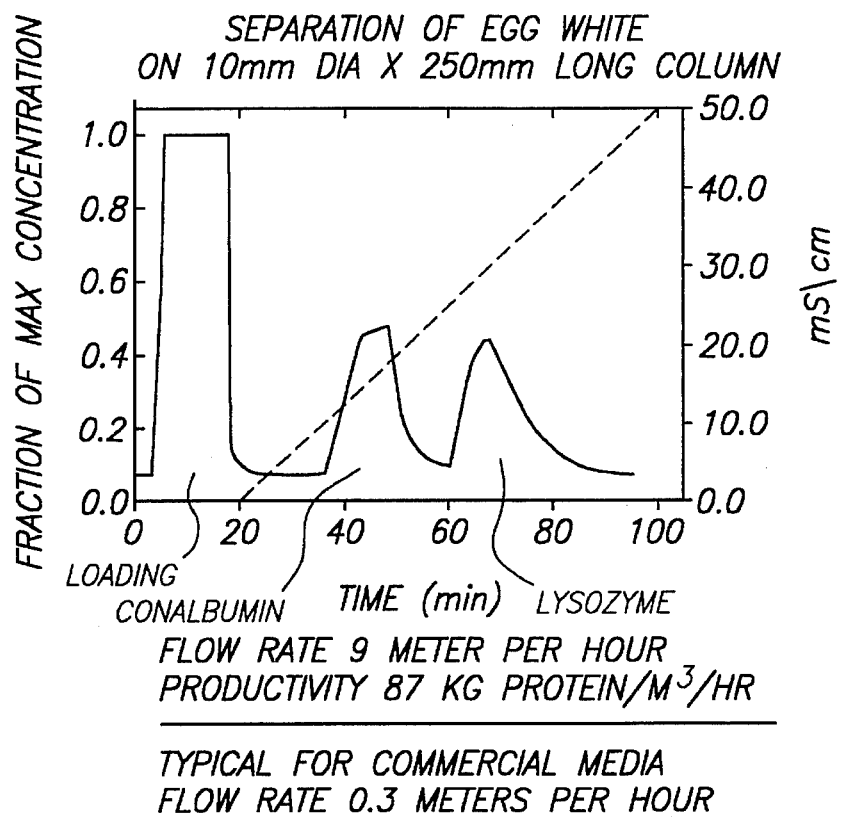
FIG. 5 is a graph showing the resulting loading and elution profile according to Example 6 of the specification.

130 ml of 14 mg/ml of fresh egg white of pH 4.8 and ionic strength of 2.3 ms/cm is fed to a bed of the CM-porous sponge media contained in a column of 250×10 mm diameter and recycled 18 times through the column. After washing the column with loading buffer of 0.01M sodium acetate at pH 4.8 for 3 minutes, elution of the conalbumin and lysozyme was effected with a salt gradient using 250 ml of 0.6M sodium chloride solution and 250 ml of 0.01M sodium acetate buffer at pH 4.8 at a flow rate greater than 9 meters/hr. The resulting loading and elution profile are illustrated in FIG. 5.

This example shows that high resolution separations can be achieved at fast flow rates using a sponge adsorbent medium with primary pores which make it suitable for commercial scale operation.

EXAMPLE 7

Figure 6:
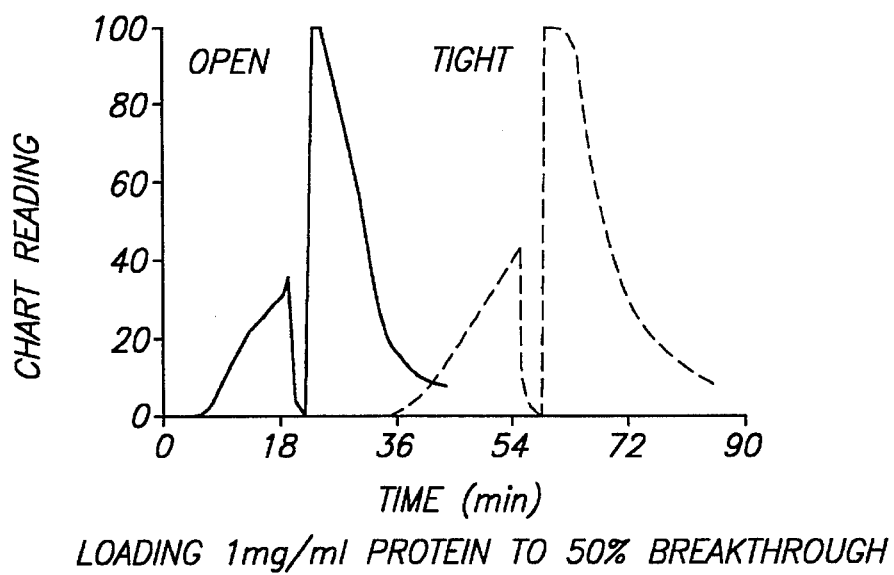
FIG. 6 is a graph showing the results of a comparison drawn between two carboxymethyl derivatives according to Example 7 of the specification.

In this Example a comparison is drawn between two carboxymethyl derivatives prepared as in Example 2, the first derivative being prepared from viscose having primary pores in the range 1500 to 3000 microns (as produced according to Method 1 of Example 1) and the second derivative being prepared from viscose having primary pores in the range 250 to 500 microns respectively (as produced according to Method 3 of Example 1). The results of the experiment are shown in FIG. 6.

In both cases the CM-Porous sponge media was packed into a column of 20×25 mm diameter and a 0.01M sodium acetate buffer solution, at pH 4.5, containing 1 mg/ml of lysozyme, was pumped through the columns at a flow rate of 4 meters per hour until the lysozyme concentrate in the output was 50% of that at the input of the column. The quality of resolution was similar in both cases. The time required to reach the breakthrough point was three times longer for the small pore structure compared to that for the larger pore structure. This is considered to be because of greater capture efficiency and higher density. In both cases a high flow rate which was considered to be superior to that which could be obtained with particulate material was maintained. To illustrate the amount of bound lysozyme the latter was eluted from the column in a single step with carbonate buffer at pH 9.

EXAMPLE 8

This example demonstrates the use of compression of a porous adsorbent medium to concentrate a dilute protein solution during an adsorption process. A 320 times concentration factor of the protein solution was achieved.

Cross-linked porous cellulose sponge was prepared according to Method 4 of Example 1. The sponge had a porous structure with primary pores in the range 1000 to 3000 microns and was converted to make CM cellulose porous sponge according to the method of Example 2. The sponge was then cut into a disc of dimensions 5 mm×25 mm diameter and inserted into a small column. 1500 ml of lysozyme at a concentration of 0.1 mg/ml in 50 mM acetate buffer at pH 4.5 was then recirculated through the disc at a flow rate of 36 m/hr for 30 minutes. The disc was then washed with at least 10 times the disc volume of loading buffer and mechanically squeezed to remove excess buffer. 2.5 ml of 0.25 mM sodium carbonate, pH 10.6 buffer was added to saturate the disc. After five minutes the elution buffer was mechanically squeezed from the disc and collected; the buffer contained lysozyme at a concentration of 32 mg/ml.

EXAMPLE 9

This example shows that an adsorbent medium produced by a method according to the present invention comprises channels having a greater proportion by volume of the medium than do the corresponding channels of a particulate adsorbent material. This is an important reason why an adsorbent medium produced by a method according to the present invention has superior flow characteristics compared to known particulate materials.

A comparison is drawn between the total pore volume and the voidage (the primary pore volume/the space between particles) for CM cellulose sponge, Pharmacia Fastflow Sepharose CM, Whatman CM52 and High capacity Phoenix CM. A column of height 50 mm and diameter 10 mm containing the respective adsorbent material was set up in each case and size exclusion data determined using 0.5% acetone and 0.9 g of blue dextran (molecular weight at 2,000,000). 0.25 ml of each of these solutions was injected into the stream of a column flowing with water at a flow rate of 0.35 ml/min. The values for acetone show the total void volume and the values for blue dextran the fractional voidage. The results are shown in the following table.

| Porous Vol. | Acetone % | Blue Dextran % |
| --- | --- | --- |
| Sponge Adsorbent Medium (produced by a method according to the present invention) | 94 | 69 |
| Pharmacia | 94.5 | 43 |
| Whatman | 82 | 25 |
| Phoenix | 92.5 | 23 |

EXAMPLE 10

This example demonstrates the superior flow rate and kinetic properties of a sponge adsorbent medium according to the present invention as compared to those properties of a particulate medium. A single protein, Human Serum Albumin (HSA), is studied for simplicity. The maximum capacities (Qm) and dissociation constants (Kd) were determined for Pharmacia Fastflow DE Sepharose and quaternary methyl ammonium (QMA) sponge as prepared in Example 4. The results were: for the Pharmacia Sepharose, Qm=98 g/l and Kd=0.2 mg/ml; for the sponge Qm=19 g/l and Kd=0.04 mg/ml.

In most large scale commercial processes the product of interest is often present at a concentration of approximately 1 mg/ml. In order to test the relative potential productivities a solution of HSA at 1.0 g/l was loaded onto columns of similar capacity containing Pharmacia Sepharose and the sponge adsorbent medium respectively. The column containing the Pharmacia Sepharose was loaded and eluted at a flow rate of 0.3 m/hr, with 1 g/l of the HSA in 0.05 M Tris based buffer at pH 7.5 and a 0.05 M sodium acetate buffer at pH 4.5 respectively. A potential productivity of 19 Kg/m$^3$/hr at yields of 84% and an eluted concentration of 5.2 g/l was achieved.

A similar experiment was carried out using the adsorbent sponge except that the column was loaded using feed recirculation at a velocity of 9.2 m/hr. A potential productivity of 40 kg.m$^3$/hr at a yield of 95% and an eluted concentration of 4.8 g was achieved.

EXAMPLE 11

In order to illustrate the effect of the fibrous reinforcement, samples of sponge with and without fibrous reinforcement were made according to Example 1. The compressive modulus was then measured in a fully saturated condition after immersing the sponge in distilled water for 48 hours. The compressive modulus for the non reinforced material was 0.2 MPa whereas that for the reinforced material was 2 MPa. The non reinforced sponge was considered too compressible for its proposed use and deteriorated easily during attempts to further process it.

EXAMPLE 12

This example shows how the properties (e.g. total void volume, fractional voidage and primary pore wall thickness) of a regenerated cellulose sponge are dependent on the components present in the solution of sponge forming material from which the cellulosic sponge is regenerated.

Four viscose samples were produced according to Example 1, the composition of each viscose sample is shown in the following table. Each viscose sample was regenerated and cross-linked according to methods 1 and 3 of Example 1 respectively. The quantity of hydrated sodium sulphate and cotton linters used in the regeneration of the viscose was varied for each viscose sample.

The following table illustrates the individual compositions and properties of each viscose sample.

| Sample | 1 | 2 | 3 | 4 |
|---|---|---|---|---|
| Components present in the solution from which the cellulose sponge is regenerated | | | | |
| Cellulose % | 1.5 | 1.5 | 3.0 | 3.0 |
| Cotton Linters % | 0.5 | 0.5 | 1.0 | 1.0 |
| Sodium Sulphate % | 76 | 60 | 76 | 60 |
| Total Void Volume % | 94 | 91 | 86 | 83 |
| Fractional Voidage % | 69 | 51 | 65 | 50 |
| Wall Thickness (microns) | 20 | 47 | NT | NT |

The main effect of lowering the quantity of hydrated sodium sulphate present in the polymeric solution is to reduce the voidage of the resultant cellulose sponge medium.

Increasing the quantities of cellulose and fibrous reinforcement in the polymeric solution decreases the total porous volume of the cellulose sponge adsorbent medium. Sample 1 was considered suitable for the adsorption of macromolecules. Sample 4 however could be substituted to give the highest ion exchange capacity per unit volume and was most suitable for the adsorption of small mineral ions.

We claim:

1. A method of preparing a controlled pore size, cross-linked, flexible, sponge adsorbent medium comprising the steps of:
    a) mixing cellulose, sodium hydroxide and water;
    b) preparing viscose from the mixture in step a);
    c) adding sodium sulfate and calcium carbonate particles and cotton linters to the mixture in step b);
    d) contacting the mixture in step c) with a cross-linking agent to form cross-linked cellulose;
    e) contacting the solution in step d) further with alkali to solubilize non cross-linked cellulose; and
    f) regenerating the cross-linked cellulose in step e) in sodium sulfate solution.

2. The method of claim 1 wherein said cross-linking reagent is selected from the group consisting of formaldehyde, dichlorhydrin, epichlorhydrin, dibromomethane, bisepoxypropyl ether, 1,4-butane diol-bis-epoxy ether, glyoxal, and divinylsulphone.

3. The method of claim 2 wherein said cross-linking agent is dichlorhydrin.

4. The method of claim 2 wherein said cross-linking agent is epichlorhydrin.

5. The method of claim 1, where in the particle size of said sodium sulfate is in the range of 200 to 400 microns and the particle size of said calcium carbonate is less than 2 microns.

6. The method of claim 1, wherein the particle size of said sodium sulfate is in the range of 1000 to 3000 microns and the particle size of said calcium carbonate is less than 2 microns.

7. The method of claim 2, wherein the product in step f) is further contacted with a solution containing a reagent which introduces an ion-exchange group into the cross-linked flexible sponge.

8. The method of claim 7 wherein said reagent is chlorohydroxy propane sulfonic acid.

9. The method of claim 2 wherein said reagent is a mixture of chlorohydroxy propyl trim ethyl ammonium chloride and sodium borohydride.

10. The method of claim 2 wherein said reagent is an alkaline mixture of sodium chloroacetate.

* * * * *